(12) United States Patent
White

(10) Patent No.: US 6,225,128 B1
(45) Date of Patent: May 1, 2001

(54) COLOR TEST CARD PACKAGE FOR TESTING FOR THE PRESENCE OF LEAD

(75) Inventor: Kenneth T. White, Virginia Beach, VA (US)

(73) Assignee: WRS and Associates, Norcross, GA (US)

( * ) Notice: Subject to any disclaimer, the term of this patent is extended or adjusted under 35 U.S.C. 154(b) by 0 days.

(21) Appl. No.: 09/253,224

(22) Filed: Feb. 19, 1999

(51) Int. Cl.[7] .......................... G01N 31/22; G01N 33/20
(52) U.S. Cl. ........................ 436/77; 436/73; 422/61
(58) Field of Search ................. 436/77, 73, 8; 422/61, 68.1, 119, 82.05

(56) References Cited

U.S. PATENT DOCUMENTS

| | | | |
|---|---|---|---|
| 1,634,183 | * 6/1927 | Gervais et al. | 73/864.01 |
| 3,870,469 | * 3/1975 | Walker | 23/232 |
| 3,893,808 | * 7/1975 | Campbell | 23/253 |
| 4,873,197 | * 10/1989 | Gould | 436/77 |
| 5,039,618 | * 8/1991 | Stone | 436/77 |
| 5,330,917 | * 7/1994 | Stone | 436/73 |
| 5,492,835 | * 2/1996 | Koenig | 436/77 |
| 5,558,835 | * 9/1996 | Kozarsky et al. | 422/56 |
| 6,001,658 | * 12/1999 | Frederickson | 436/514 |

* cited by examiner

*Primary Examiner*—Jill Warden
*Assistant Examiner*—La Toya I. Cross

(57) ABSTRACT

A package comprises a sealed plastic envelope containing a small amount of desiccant sufficient to absorb the moisture in the air entrapped in the envelope. The package contains a dry test card having at least one circular area coating of a dry solid rhodizonic acid dipotassium chromogen salt free of any solvent.

2 Claims, 1 Drawing Sheet

COLOR TEST CARD PACKAGE FOR TESTING FOR THE PRESENCE OF LEAD

BACKGROUND OF THE INVENTION

U.S. Pat. No. 4,873,197 and 5,010,020 disclose processes for quick color tests for detecting the presence of lead in glaze and enamel coatings as well as kits which can be used in making such tests. To this end, a sample is first washed with a detergent. The surface of the sample is then contacted with a slip of filter paper wet with a solution of citric or formic acid. After a suitable time period, the paper slip is spotted with a liquid chromogen. The formation of a rose or rose/red stain signifies that the tested coating has an releasable amount of lead. A suitable test kit for performing such tests consists of absorbent paper strips, an aqueous solution of a suitable acid, distilled water and a rhodizonic acid dipotassium salt. The salt is deliquescent and deteriorates in air in the presence of moisture and must be dissolved in the water just before used as a liquid.

After it was recognized that excess lead in painted surfaces could also be harmful, it was found that neither the kit nor the test described above could be used without modification to identify the presence or absence of lead in painted surfaces. Accordingly a new test and suitable kit were developed.

This kit employs a non-porous card having one or more small sections with circular coatings of a solid rhodizonic acid dipotassium salt chromogen. In use, the tip of a cotton swab is charged with a liquid acid and a small sample of the painted surface being tested and then is moved into contact with this chromogen coating to test for the presence of lead. When the chromogen coating is in proper condition, the color change of this chromogen indicates the presence of lead. The coatings of the rhodizonic salt are prepared by dissolving the salt and a sodium acetate buffer in water then immediately applying this solution to the card as a coating which is then dried. The card is packaged inserted in the package. However, because of unpredictable variations in the moisture content and the absorbent properties of the desiccant, this package has a variable and unpredictable useful life since the chromogen coating may be contaminated with entrapped moisture. Thus the useful life of this kit is also variable and unpredictable.

The present invention is directed toward a package containing a card with coatings of a rhodizonic salt which is not contaminated with water and thus is more stable and less variable as well as a process for producing this card.

SUMMARY OF THE INVENTION

It is an object of this invention to provide a new and improved process for applying a rhodizonic salt coating to a card using an alcohol rather than water as a solvent whereby the solvent can be completely evaporated as the card is dried.

Another object is to package the solvent free and completely dried rhodizonic salt coated card in a sealed plastic envelope containing a desiccant whereby the card can be stored for use and remains completely dry and ready for use when removed from the envelope.

These and other objects and advantages of the invention will either be explained or will become apparent hereinafter.

In accordance with the principles of this invention, a liquid mixture of solid rhodizonic acid dipotassium salt chromogen dissolved in an alcohol solvent is pipetted onto a semi-dry test card to form one or more circular coated areas. The alcohol solvent immediately begins to evaporate and the coating begins to dry. The coated card is then placed in a microwave oven and is heated to drive off any entrained air moisture as well as any solvent remnant. The heating process is continued until just before the card begins to char. The still warm dry card is then immediately inserted in a plastic envelope and sealed. The envelope also contains a small amount of desiccant which is only necessary to absorb any water moisture contained in the air in the envelope at the instant when the card is inserted so that the card remains completely dry and the solid rhodizonic acid dipotassium salt chromogen coating can be immediately used successfully as soon as the card is removed from the package. As long as the package remains sealed, it retains its useful life and the card once removed does not display the erratic behavior of moisture contaminated chromogen coatings.

DETAILED DESCRIPTION OF PREFERRED EMBODIMNT

Figure 1:
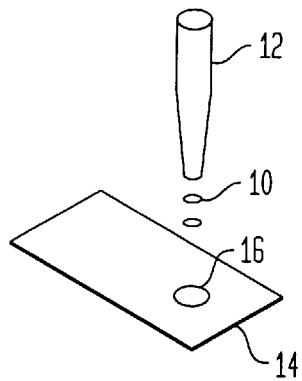
FIGS. 1 and 2 illustrates the process for producing cards containing chromogen coatings in accordance with the principles of the invention.
Figure 2:
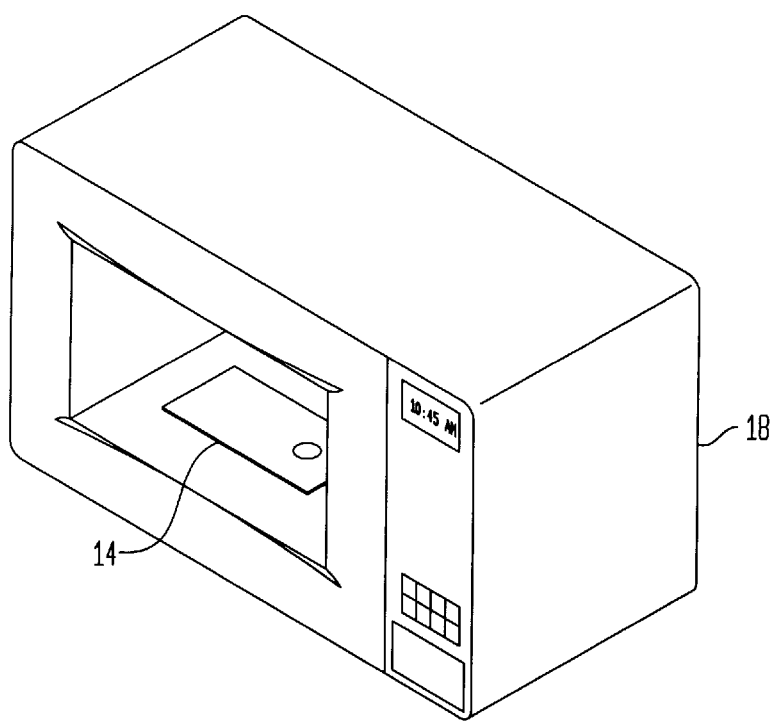
Figure 3:
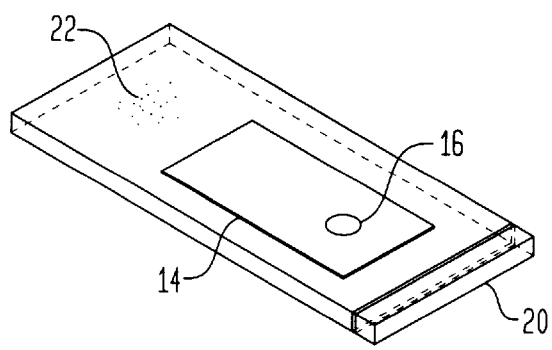
FIG. 3 illustrates the final package.

Referring now to FIGS. 1 and 2, drops 10 of solid rhodizonic acid dipotassium salt chromogen powder dissolved in isopropanol alcohol are fed through a pipette 12 to a flat dry cardboard card 14 to form one or more spaced circular coatings 16. Both alcohol and water begin to evaporate as the drops are formed However, the alcohol, evaporates faster than water. The coated card, or if desired a plurality of such cards, is then placed flat in a microwave oven 18 and is irradiated to a temperature for a time just below that at which the card begins to char.

The card is then inserted into a plastic envelope 20 together with a small amount of desiccant 22. The desiccant is used only to absorb the small amount of moisture entrapped within the envelope. The card is sealed in dry condition as previously explained.

While the invention has been described with particular reference to the drawings and detailed description, the protection solicited is to be limited only by the terms of the claims which follow.

What is claimed is:

1. A method for producing a color test card for visually indicating the presence or absence of lead in material applied thereto, said method comprising the steps of:

dissolving a solid rhodizonic acid dipotassium chromogent salt in an alcohol solvent to produce a liquid mixture of salt and solvent;

feeding said mixture drop by drop through a pipette onto a flat dry test card to form at least one circular area of a coating of said mixture while the solvent is evaporating;

heating said card in a microwave oven to drive off any entrained air moisture as well as any solvent remnant, the heating process being continued until just before the card begins to char; and inserting the dried coated card with a small amount of desiccant into a plastic envelope which is immediately sealed, this amount being only necessary to absorb any water moisture contained in the air at the instant when the card is inserted so that the card remains completely dry.

2. A package comprising a sealed plastic envelope containing a dry test card having at least one circular area coating of a dry solid rhodizonic acid dipotassium chromogent salt free of any solvent, said envelope also containing a small amount of desiccant, this amount being only necessary to absorb any water moisture contained in the air at the instant when the card is inserted in the envelope so that the card remains completely dry.

* * * * *